(12) United States Patent
Arnebrant et al.

(10) Patent No.: US 6,444,321 B1
(45) Date of Patent: Sep. 3, 2002

(54) REVERSIBLY, NON-COVALENT BOUND SURFACE COATING

(75) Inventors: Thomas Arnebrant, Lund; Börje Sellergren; Aleksander Swietlow, both of Helsingborg, all of (SE)

(73) Assignee: Forskarpatent I Syd AB, Lund (SE)

( * ) Notice: Subject to any disclaimer, the term of this patent is extended or adjusted under 35 U.S.C. 154(b) by 0 days.

(21) Appl. No.: 09/077,467

(22) PCT Filed: Dec. 2, 1996

(86) PCT No.: PCT/SE96/01583
§ 371 (c)(1),
(2), (4) Date: Jul. 9, 1998

(87) PCT Pub. No.: WO97/20639
PCT Pub. Date: Jun. 12, 1997

(30) Foreign Application Priority Data

Dec. 1, 1995 (SE) .............................................. 9504347

(51) Int. Cl.[7] .............................. B32B 7/04; B32B 31/00
(52) U.S. Cl. .................... 428/420; 428/411.1; 427/399
(58) Field of Search .............................. 428/411.1, 420, 428/357, 403; 436/103–105, 169, 170, 501, 815

(56) References Cited

U.S. PATENT DOCUMENTS

| | | | | |
|---|---|---|---|---|
| 4,144,221 A | * | 3/1979 | Ikeda et al. .......... 260/33.4 SB |
| 4,895,566 A | * | 1/1990 | Lee ............... 604/266 |
| 5,106,951 A | * | 4/1992 | Morgan, Jr. et al. ..... 530/391.9 |
| 5,208,111 A | | 5/1993 | Decher et al. |
| 5,278,249 A | * | 1/1994 | Marrion ....................... 525/380 |
| 5,368,942 A | * | 11/1994 | Smith et al. ................. 428/420 |
| 5,486,603 A | * | 1/1996 | Buhr .......................... 536/24.3 |
| 5,763,276 A | * | 6/1998 | Craig et al. .................. 436/111 |
| 5,874,164 A | * | 2/1999 | Caldwell ................. 428/306.6 |
| 5,925,552 A | * | 7/1999 | Keogh et al. ............... 435/174 |
| 5,928,916 A | * | 7/1999 | Keogh ........................ 435/174 |

FOREIGN PATENT DOCUMENTS

WO     WO-9514381 A1  *  6/1995

OTHER PUBLICATIONS

"Formulation of Multilayers by Self–Assembly", Nolan Tillman et al., *Langmuir*, American Chemical Society, 1989, vol. 5, pp. 101–111.

*Biosensors and Chemical Sensors*, Peter G. Edelman et al., ACS Symposium Series American Chemical Society, 1991, pp. 1–55.

*Nucleic Acid Probes*, Robert H. Symons, Ph.D., Editor, CRC Press, Inc., Florida, 1989, pp. 1–81 and 113–160.

*Highly Selective Separations in Biotechnology*, G. Street, Editor, Blackie Academic & Professional, Chapman & Hall, London (1994) p. 1–33.

Lehn, Jean–Marie, "Perspectives in Supramolecular Chemistry–From Molecular Recognition towards Molecular Information Processing and Self–Organization", Angew. Chem. Int. Ed. Engl. 29 (1990) 1304–1319.

*An Introduction to Ultrathin Organic Films From Langmuir-Blodgett to Self–Assembly* Abraham Ulman, Academic Press, Inc., New York (1991) p. 1–83.

Kevin L. Prime et al., "Adsorption of Proteins onto Surfaces Containing End–Attached Oligo(ethylene oxide): A Model System Using Self–Assembled Monolayers", American Chemical Society (1993) 10714–10721.

(List continued on next page.)

Primary Examiner—Shrive P. Beck
Assistant Examiner—Elena Tsoy
(74) Attorney, Agent, or Firm—Burns, Doane, Swecker & Mathis LLP

(57) ABSTRACT

A surface coating and its use in chemical analysis, electronics, and optoelectronics is disclosed. The surface coating is characterized in that it comprises an amphiphile reversibly bound to a substrate by non-covalent interaction, preferably by polar interaction. The amphiphile is a bolaamphiphile, such as pentamidine.

15 Claims, 3 Drawing Sheets

OTHER PUBLICATIONS

Darryl Y. Sasaki et al., "Specific, Multiple–Point Binding of ATP and AMP to a Guanidinium–Functionalized Monolayer", American Chemical Society (1991) 9685–9686.

Israel Rubinstein et al., "Ionic Recognition and Selective Response in Self–Assembling Monolayer Membranes on Electrodes", Nature (1988) 332, 426–7.

Larry J. Kepley et al., "Selective Surface Acoustic Wave–Based Organophosphonate Chemical Sensor Employing a Self–Assembled Composite Monolayer: A New Paradigm for Sensor Design", Anal. Chem. (1992) 64, 3191–3193.

K.D. Schierbaum et al., "Molecular Recognition by SelfAssembled Monolayers of Cavitand Receptors", Science (1994) 265, 1413–1415.

W. Müller, "Attempts to Mimic Docking Processes of the Immune System: Recognition–Induced Formation of Protein Multilayers", Science (1993) 1706–1708.

George M. Whitesides, "Organized Molecular Assemblies", Crit. Rec. Surf. Chem. (1993) 3, 49–65.

Marc D. Porter et al., "Spontaneously Organized Molecular Assemblies. 4. Structural Characterization of n–Alkyl Thiol Monolayers on Gold By Optical Ellipsometry, Infrared Spectroscopy, and Electrochemistry", J. Am. Chem. Soc. (1987) 109, 3559–3568.

Ralph G. Nuzzo et al., "Adsorption of Bifunctional Organic Disulfides on Gold Surfaces", J. Am. Chem. Soc. (1983) 105, 4481–4483.

Guang Cao et al., "Layered Metal Phosphates and Phosphonates: From Crystals to Monolayers", Acc. Chem. Res. (1992) 25, 420–427.

Quan Li et al., "Chromophoric Self–Assembled Multilayers. Organic Upperlattice Approaches to Thin–Film Nonlinear Optical Materials", J. Am. Chem. Soc. (1990) 112, 7389–7390.

Gero Decher et al., "Buildup of Ultrathin Multilayer Films By a Self–Assembly Process, 1 Consecutive Adsorption of Anionic and Cationic Bipolar Amphiphiles on Charged Surfaces", Macromol. Chem., Macromol. Symp. (1991) 46, 321–327.

Nobuo Kimizuka et al., "Self–Organization of Bilayer Membranes from Amphiphilic Network of Complementary Hydrogen Bonds", J. Am. Chem. Soc. (1993) 115, 4387–4388.

R. Drmanac et al., "DNA Sequence Determination by Hybridization: A Strategy fro Efficient Large–Scale Sequencing", Science (1993) 260, 1649–1652.

"News and Views" Science (1994) 265, 2008, 2085, and 2096.

Hongbo Su et al., "Interfacial Nucleic Acid Hybridization Studied by Random Primer $^{32}P$ Labeling and Liquid–Phase Acoustic Network Analysis", Anal. Chem (1994) 66, 769–777.

Dialog Information Services, File 144, Pascal, Dialog Accession No. 12436710, Pascal Accession No. 96–0093004, Sellergren B. et al.: "Consecutive selective adsorption of pentamidine and phosphate biomolecules on a self–assembled layer: reversible formation of a chemically selective coating". Analytical chemistry:(Washington), 1996, 68(2) 402–407.

Dialog Information Services, File 144, Pascal, Dialog Accession No. 12421714, Pascal Accession No. 96–0076208, Qingxia Liu et al.: "Self–assembled monolayer coatings on nanosized magnetic particles using 16–mercaptohexadecanoic acid". Langmuir, 1995, 11(12) 4617–4622.

"Introduction to Collaid and Surface Chemistry", Duncan J. Show, $3^{rd}$ edition., Butterworth, 1980, p. 72, lines 5–8.

* cited by examiner

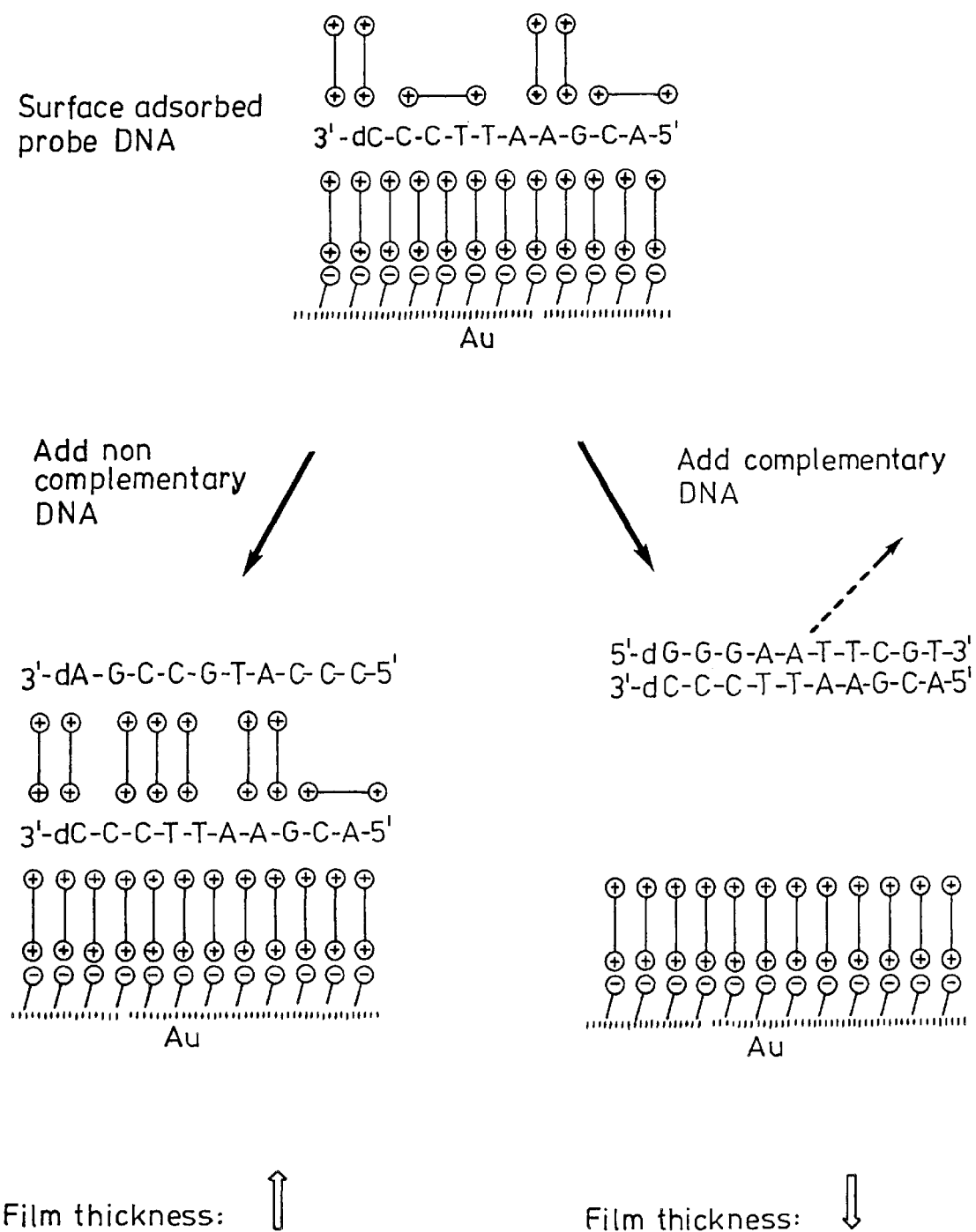

REVERSIBLY, NON-COVALENT BOUND SURFACE COATING

TECHNICAL FIELD

The present invention relates to layered surfaces and more particularly to a surface coating.

BACKGROUND

Molecular recognition and functional group complementarity are essential in the design and preparation of chemical or biological sensors,[1] affinity chromatographic supports[2] or in the build-up o organized supramolecular structures.[3] New approaches to introduce molecular selectivity in these areas are thus of potential interest.

In this context organic thin films, formed by molecular self assembly, are presently being extensively studied.[4] These can be prepared by the classical Langmuir Blodgett (LB) technique whereby a surfactant monolayer formed at the air water interface are transferred onto a solid flat surface, or by spontaneous sorption of an active surfactant onto a flat solid surface directly from solution. These processes lead to organized layers where the surfactants are held together by strong lateral interactions and stabilized by terminal covalent or polar bonds to the surface.

Chemical Sensors

As model systems for chemical sensors the above-mentioned organic films present a number of advantages:

1) The high degree of order attainable in such systems allows a good control of the surface properties (polarity, hydrophobicity, acidity etc.) so that adsorption of a certain class of compounds can be either minimized (nonspecific protein adsorption) or maximized.[5]
2) A number of signal transduction techniques are available (based on i.e. optical. electrochemical or microgravimetric measuring principles) allowing real time observation of surface processes.[4]
3) Small sensing elements can be prepared using the lithographic technology available in the preparation of IC:s. Miniaturisation is an important factor in sensor design.
4) Surfaces can be rationally designed whereby analyte specific ligands or hosts are incorporated into the layers. This allows specific molecular recognition that can be monitored in real time.[6,7,8]

Simple chemical strategies to introduce selectivity are desirable from the aspects of stability and ease of preparation. Kunitake et al[7] demonstrated that self-assembled guanidinium amphiphiles It the air water interface could be used for selective adsorption of adenosine-phosphates. The binding of ATP was believed to involve three guanidinium groups bound by hydrogenbonded ion pairs to the phosphate groups of ATP. Transferring thee layers by Langmuir-Blodgett techniques to a solid surface was suggested as a possible approach to sensor fabrication for phosphate biomolecules. However the limited stability of LB films are often a problem. The use of stable chemisorbed monolayers on flat surfaces is therefore becoming more important due to inherent advantages such as stability, ease or fabrication, order and miniaturization possibilities. Of these, particularly SAM:s formed by chemisorption of thiols on gold surfaces[9] have been extensively studied. Exposing a Au (111) surface to a dilute alkylthiol solution results in rapid formation of a hexagonally packed all trans alkyl layer characterized by stable gold-sulphur bonds and a tilt angle between the gold surface and the alkyl chains of approximately 30°. A number of different functionalities can be chosen. In the fabrication of analyte selective interfaces the coatings are often irreversibly anchored to the sensor interface preventing regeneration of the coating. In the case of strongly bound analytes this may limit the reusability of the surface. Chemically selective coatings that can be reversibly attached to a sensor interface would in 1his context be of interest.

Multilayered Structures

Multilayers with ordered structures are presently the focus of intense research due to emerging applications in optoelectronics (telecommunications), molecular electronics and chemical sensing.[4,10] These can be achieved by incorporating functional units (dipoles, donor acceptor pairs, chromophores) into the hydrophobic part of the amphiphile. Due to stability problems of the resulting multilayers new alternative techniques need to be developed. The spontaneous self-assembly strategy is becoming increasingly popular. In this, usually two biofunctional building blocks, complementary to each other are repeatedly allowed to self-assemble on a solid substrate. In one such system, Decher et al described a strategy for multilayer formation based on consecutive adsorption of alternately charged bolaamphiphiles (amphiphiles containing two terminal polar groups) and polyelectrolytes.[10d] This allows build-up of multiple layers with a total thickness of up to a few thousand Å thus giving the films bulklike properties. Furthermore these properties are ideal for non-linear optics since such a film would allow stable noncentrosymmetric orientation of polarizable dipoles. One goal in the construction of these films is to reduce the interlayer spacing and thereby to achieve a higher density of the functional units. Unfortunately this has a destabilizing influence on the formed layers. The building blocks (amphiphiles) are in these instances therefore larger than 30 Å. Systems based on strong directed headgroup interactions would allow smaller amphiphiles to be used.

Gene Analysis

Routine gene analysis rely on the detection of specific DNA or RNA sequences present in minute amounts in a complex mixture. The current analytical methods usually involve time-consuming labelling and separation steps.[11] and have therefore become a bottleneck in areas that depend on rapid DNA sequencing (i.e. HUGO, forensic analysis, diagnostics). Alternative methods for direct rapid sequencing are therefore being developed These often involve the use of presynthesized probe oligonucleotides capable of hybridizing specifically to the sequence of interest.[12] An attractive approach is the direct monitoring (i.e. by optical, electrochemical or gravimetrical signal transduction) of the hybridization event using the probes attached to a solid surface (FIG. 3).[13] Particularly intriuging is the combination of these methods with microlithography allowing the preparation of arrays of different probe sequences that each would represent a separate sensing element. In the above-mentioned systems however the probe is usually covalently linked to the support requiring additional chemical steps. Techniques for reversible attachment of the probe to the surface would be attractive for a rapid scanning of the hybridization properties of a large number of probes towards a certain target DNA.

Protein Adsorption

The behaviour of proteins at interfaces and in particular at the solid/liquid interface is of outmost importance in determining the processes taking place upon contacting a surface with a biological fluid. Therefore, knowledge of the type of proteins adsorbed and their structure (conformation) is a field of intense research within the areas of implant integration, blood compatibility and dental plaque formation. A key issue is to be able to selectively adsorb the "right proteins" in the desired conformation/orientation. Apart for varying solution conditions the major tool in this process is to tailor the surface with respect to functionality (type of groups and density). Techniques for quick and convenient control of these parameters would be a very useful instrument in optimize surface with respect to the above-mentioned applications. Similar considerations also applies for surface modification with respect to immobilization of enzymes for sensor applications.

THE PRESENT INVENTION

The present invention provides a surface coating, characterized in that it comprises an amphiphile reversibly bound to a substrate by noncovalent interaction.

According to preferred embodiments:

The amphiphile is bound to the substrate by polar interaction between cationic groups of the amphiphile and anionic groups of the substrate;

The polar interaction between the amphiphile and substrate is pH dependent;

The amphiphile is a bolaamphiphile;

The amphiphile is selected from amidines;

The amphiphile is selected from bisbenzamidines;

The amphiphile is pentamidine;

The surface coating is used in chemical separation and analysis;

The surface coating is used in electronis; and

The surface coating is used in optoelectronics.

In a particularly preferred embodiment the amphiphile is a so-called bolaamphiphile (an amphiphile having two polar groups connected by a nonpolar linking group) selected from bisbenzamidines, preferably having a linking group with about 2–14 carbon atoms and particularly pentamidine, where one of the positively charged polar amidinium groups is reversebly bound to a negatively charged group, preferably a carboxylic group of a substrate by polar interaction. The reversibility of the binding of the amphiphile to the substrate is pH dependent and related to the pK-value of the acidic groups on the substrate. Usually this pK-value lies in the range from about 2 to about 6 and is about 4.5 for carboxylic acid. In the specific case of amidines, such as pentaamidine, bound to a substrate with carboxylic groups this means that substantially all of the amphiphile (amidine) is bound to the substrate at a pH of about 7–8.5 and is released from the surface at a pH of about 3 or below.

Generally, the present invention may be used inter alia in chemical separation and analysis, in electronics and in optoelectronics. By way of example some fields of use are:

Selective adsorption of biological molecules, such as phosphate biomolecules. Particularly, this selective adsorption nay be used in chemical sensors and detector devices; Sensors based on e.g. enzymes linked to the surface in an active orientation/conformation. Hereby the sensitivity/selectivity of the sensor could be optimized. The switching capacity could be utilized for quick regeneration or substitution of the type of immobilized enzyme for other target molecules;

Enhancing or inhibiting the compatibility with biological materials, e.g. inhibiting rejection in connection with surgery; enhancing the ingrowth of bone implants;

As a dental coating for inhibiting plaque growth or to improve adhesion of dental restorative materials;

As a matrix for binding phospholipids and provide models of biological membranes;

Inhibiting the coagulation of blood by coating a surface in contact with blood in accordance with the invention so that becomes compatible with the blood;

Administration of drugs by providing the surface of a carrier with a coating according to the invention where the amphiphile binds the drug and the bond is pH dependent so that the drug is released in dependence of the pH;

The invention may also be used o surface modify any administration vessel tubing or pump in order to minimize lose of active substance due to adsorption.

Another field of use is chromatography, more particularly column chromatography where the column or its packing is coated with the surface coating according to the invention. The coating includes an amphiphile (or a substance bound to the amphiphile) with affinity to the substance to be separated by chromatography. The chromatography process could e.g. constitute a method for purification of contaminated blood, where the contaminant is bound to the coating. As mentioned above, the affinity of the coating is preferably reversible and pH dependent so that the column can be easily regenerated;

A further field of use is extraction of substances from fluids, such as gold from seawater by providing the amphiphile with affinity to the substance (gold). Again, the affinity is preferably reversible (e.g. depending on the pH) so that the extraction device may be regenerated;

Still another field of use is the analysis of DNA sequences which will be described further below.

BRIEF DESCRIPTION OF THE DRAWINGS

The invention will now be described in more detail with reference to the accompanying drawings, where:

FIG. 3 is a schematic illustration of a DNA-hybridization assay.

Figure 1:
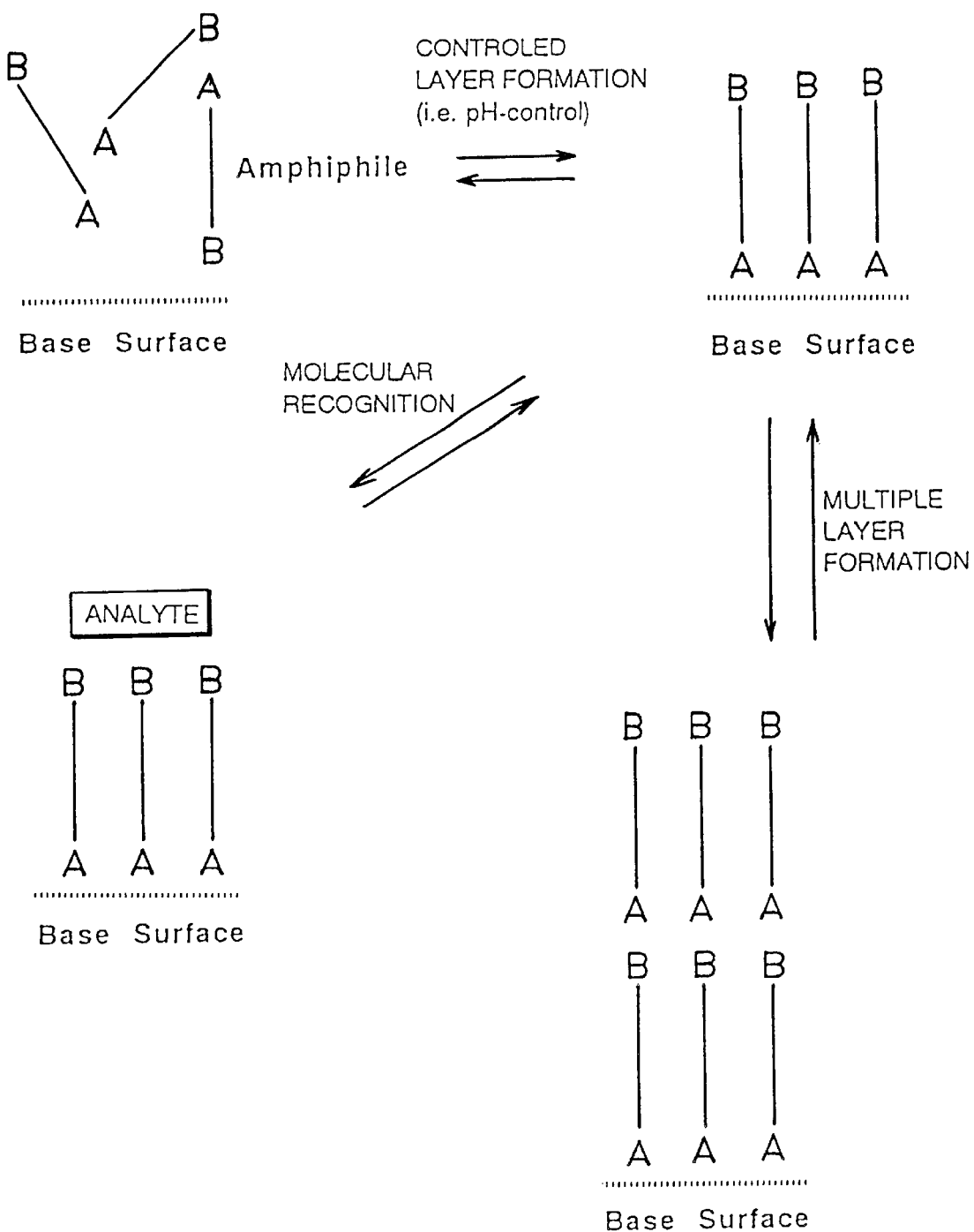
FIG. 1 is a schematic illustration of reversibly selfassembled amphiphiles on a base surface.

This invention describes a modified surface and a surface modification technique based on reversibly selfassembled amphiphiles (FIG. 1). The amphiphile, containing a polar head group (A), is able to strongly and reversibly interact by directed noncovalent bonds with an underlying surface leading to the formation of organized ordered layers. It can be equipped with another terminal functional group at the opposite end (B). The stability of the monolayer can be controlled by for instance the choice of pH in the medium. This allows a switch of the layer formation which can be used for rapid functionalization a given surface. With a proper choice of B this approach can be used to design a surface with desirable properties for instance for molecular recognition, directed crystallizations, separations or for multilayer build-up. In the multilayer build-up, the strong head group interactions allows the use of smaller building blocks than those used so far. By using different head group regioisomers can we adjust the tilt angle of the amphiphile relative to the surface. Furthermore the thickness of the layers can be adjusted to the length of the amphiphile. These properties are important in the above described optoelectronic applications.

Figure 2:
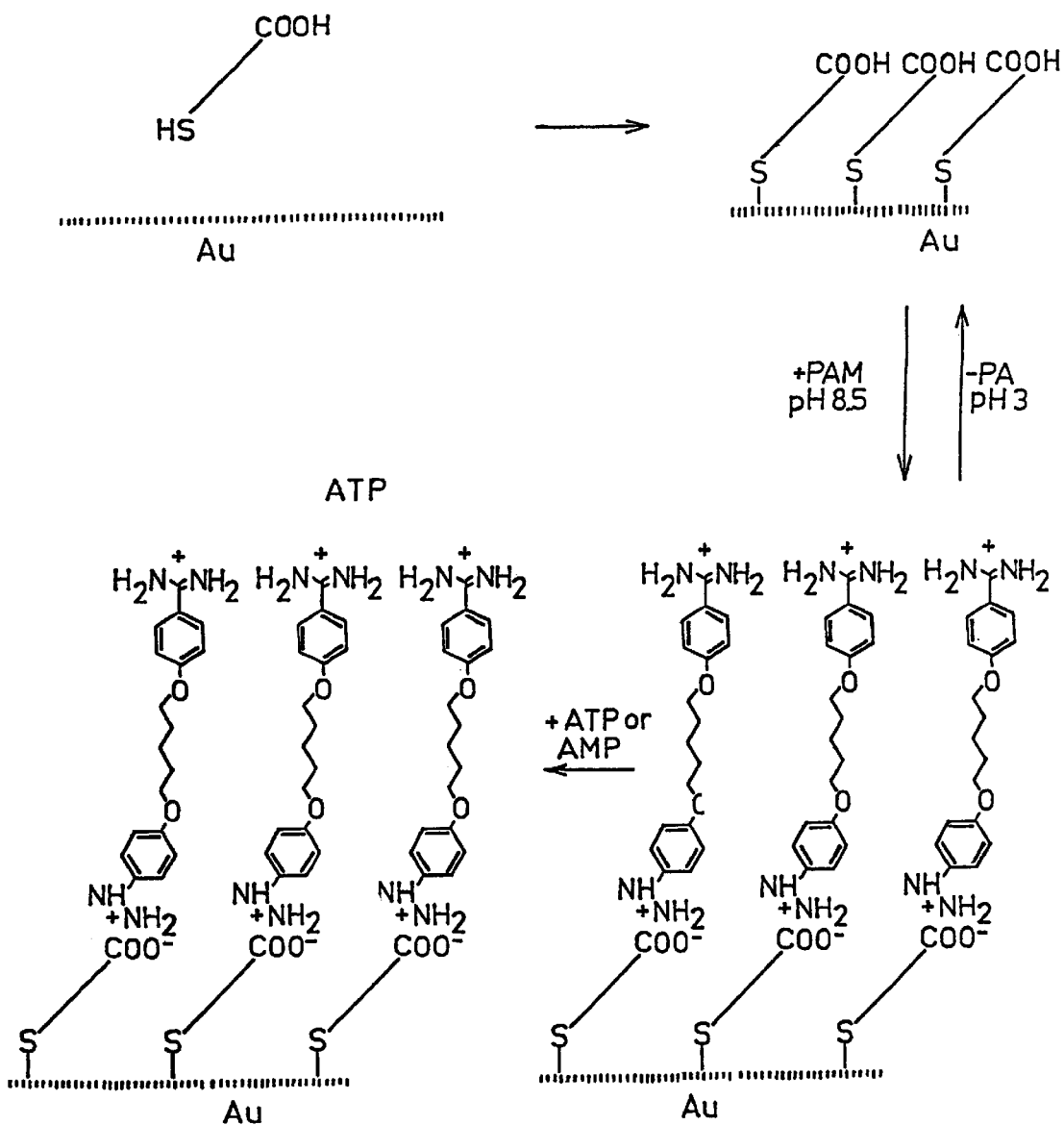
FIG. 2 is a schematic illustration of a method of providing an acidic base surface, selfassembly of a dibasic amphiphile on the acidic base surface, and binding ATP to the amphiphile.

If the amphiphile is capable of binding to nucleic acids these may be incorporated into the layer. For instance a dibasic DNA binding drug may selfassemble on an acidic surface (FIG. 2). To this transformed surface are then added a single stranded probe oligonucleotide that are reversibly bound to the surface (FIG. 3). By now adding a gene containing the target sequence an observable change in layer thickness will be observed. This process is further enhanced by the ability of such drugs to stabilize double stranded-DNA. After analysis the acidic surface is regenerated by decreasing pH and the next analysis can then take place at high pH. For a given probe sequence this technique may also be used for the study of the interaction (base specificity) between various DNA binding drugs and ds-DNA.

Changes in the surface coating layer, such as its thickness or weight may be detected by various techniques e.g. ellsometry, Surface Plasmon Resonance (SPR), quart microbalance technique (QCM), or electrochemical detection methods (e.g. impedance).

The invention will be described in more detail giving a number of nonrestricting examples.

EXAMPLE 1

Gold electrodes modified with mercaptoundecanoic acid were prepared by sorption of the thiol from a 1 mM solution of mercaptoundecanoic acid in ethanol for at least 12 h followed by rinsing with ethanol and drying under a nitrogen stream. In this way a Base surface with carboxylic groups was prepared. This process was followed ellipsometrically (Rudolf thin-film ellipsometer 43603-200 E using an angle of incidence of 68° and a HeNe laser light source, $\lambda=633$ nm). giving a thickness increase of 13 Å indicating the formation of a well packed dense monolayer. At pH 8.5 addition of a 2.5 mM aqueous solution of the dibasic drug Pentamidine (PAM) in presence of the modified electrode produced a 20% decrease in the measured double layer capacitance and a thickness increase of ca 21 Å. This indicates formation of a second well packed monolayer on top of the acid layer (PAM-surface). Addition of adenosine-triphosphate (ATP) to the PAM-surface gave an additional thickness increase of ca 15 Å. Addition of Adenosine-monophosphate gave no increase in the film thickness (see FIG. 2).

EXAMPLE 2

The PAM-surface described in Example 1 can be removed by lowering the pH to 3 whereby the thickness decreases corresponding to the PAM layer thickness. By again increasing pH the thickness increases to the original value indicating a reversible layer formation. No increase in film thickness is seen when adding ATP or AMP at low pH.

EXAMPLE 3

Gold electrodes modified with mercaptopropionic acid were prepared by sorption of the thiols from an ethanol solution (Base surface). At pH 8.5 addition of the dibasic drug Pentamidine (PAM) in presence of the modified electrode produced a thickness increase of 13 Å. This indicates formation of a second monolayer on top of the acid layer (PAM-surface). Addition of adenosine-triphosphate (ATP) to the PAM-surface gave an additional thickness increase of ca. 20 Å. Addition of Adenosinemonophosphate gave no increase in the film thickness.

EXAMPLE 4

The PAM-surfaces prepared for instance as in Example 1 and 3 can be used for molecular recognition of other phosphate containing molecules (NAD cofactors, oligonucleotides, nucleotide-triphosphates, inositolphosphate, phosphoproteins etc.). For instance addition of inositoltetraphosate gave an additional thickness increase of 20 Å whereas inositoldiphosphate only gave a thickness increase of ca. 10 Å. Phosphorylated proteins can be analyzed in this way.

EXAMPLE 5

The layer thickness can be adjusted to the size of the amphiphile. For instance in the serie ethamidine (18 Å), pentamidine(21 Å), octamidine (26 Å) were the measured thicknesses close to the molecular size.

EXAMPLE 6

The PAM surfaces such as those described in Example 1 and 3 are able to bind oligonucleotides giving larger thickness increases (FIG. 3). An oligonucleotide containing 10 bases gave thus a thickness increase of up to 30 Å. This layer thickness is zero at pH 2 and reproduced after a return of the pH to pH 8.5.

EXAMPLE 7

By adding a gene, containing a sequence of nucleotide bases that is to be detected, to the complementary probe modified surface described in Example 5 a decrease in layer thickness was observed (FIG. 3). This was only observed when the probe and the gene were fully complementary. Thus using a probe containing one or several mismatches to the target sequence, an continuing increase in layer thickness was observed.

EXAMPLE 8

Surface according to EXAMPLE 1 but where the amphiphile is the aromatic bisamidine ethamidine. This surface gave a smaller thickness increase when adding an oligonucleotide.

EXAMPLE 9

Use of the technique for the build-up of DNA multilayers. Using octamidine and a 10 mer of thymidine a total thickness of 80 Å was observed.

EXAMPLE 10

Gold electrodes modified with mercaptohexadecanoic acid (MHA) were prepared by adsorption of the thiols from ethanol solution. Addition of decamidine (DAM) to this surface produced an ellipsometrically determined increase in thickness of 50 Å.

Adsorption of the positively charged protein lysozyme at pH 7.8 followed by rinsing with pure borate buffer caused an additional increase by 30 Å. The corresponding increase in thickness upon ad sorption to the pure MHA surface was 55–60 Å.

For comparison, adsorption of the negatively net charged protein fibrinogen at pH 8.8 gave thickness increases after adsorption and buffer rinsing of 75 Å to the MHA-DAM surface and 48 Å to the pure MHA surface.

Thus, the affinity of the above surface coating of the invention (in comparison to the unmodified MHA surface) is different for different proteins, and higher for fibrinogen than for lysozyme.

[1] *Biosensors and Chemical Sensors,* Edelman, P. G.; Wang, J. Eds., ACS Symp. Ser. 487, Washington DC, American Chemical Society, 1992

[2] *Highly Selective Separations in Biotechnology,* Street, W. Ed. Chapman and Hall, 1993.

[3] Lehn, J. -M. *Angeii,. Chem. Int. Ed Eng* 1990, 29, 1304.

[4] Ulman, A. *An Introduction to Ultrathin Organic Films from Langmuir-Blodgett to Self-assembly;* Academic Press, Inc.; New York, 1991.

[5] Prime, K. L; Whitesides, G. M. *J. Am. Chem. Soc.* 1993, 115, 10714

[6] Sasaki, D. Y.; Kurihara, K.; Kunitake, T. *J. Am. Chem. Soc.* 1991, 113, 9685–9686.

[7] (a) Rubinstein, I.; Steinberg, S.; Tor Y.; Shanzer, A.; Sagiv, J. *Nature* 1988, 332. 426–429. (b) Kepley, L. J.: Crooks, R. M.; Ricco, A. J. *Anal. Chem.* 1992, 64, 3191–3193. (c) Schierbaum, K. D.; Weiss, T.; Thoden van Velzen, E. U.;Engbersen, J. F. J.; Reinhoudt, D. N., Göpel, W. *Science* 1994, 265, 1413–1415.

[8] Müller, W.; Ringsdorf, H.; Rump. E., Wildburg, G.; Zhang, X.; Angernaier, L.; Knoll, W.; Liley, M.: Spinke, J. *Science* 1993, 262, 1706–1708.

[9] (a) Whitesides, G. M.: Ferguson, G. S.; Allara, D.; Scherson, D.; Speaker, L.; Ulman, A. *Crit. Rev. Surf Chem.* 1993, 3, 49–65 (b) Porter, M. D.; Bright, T. B.; Allara, D. L.; Chidsey, C. E. D. *J. Am. Chem. Soc.* 1987, 109, 3559–3568. (c) Nuzzo, R. G.; Allara, D. L. *J. Am. Chem. Soc.* 1983, 105,4481–4483.

[10] (a) Cao, G.; Hong. H.- G.; Mallouk, T. E. *Acc. Chem. Res.* 1992, 25, 420–427, and references therein. (b) Tillman, N.; Ulman, A.; Penner, T. L . *Langmuir* 1989, 5, 101. (c) Li, D.; Ratner, M. A.; Marks, T. J.; Zhang, C.; Yang, J.; Wong, G. K. *J. Am. Chem. Soc.* 1990, 112, 7389–7390. (d) Decher, G.: Hong, J. -D. *Macromol. Chem., Macromol. Symp.* 1991, 46, 321–327. (e) Kimizuka, N.; Kawasaki, T.; Kunitake , T. *J. Am. Chem. Soc.* 1993, 115, 4387–4388.

[11] (a) Drmanac, R.: Drmanac, S.; Strezosa, Z.; Paunesku, T.; Labat, I.; Zeremski, M.; Snoddy, J.; Funkhouser, W. K.; Koop. B ; Hood, L.; Crkvenjakov, R. *Science* 1993, 260, 1649 (b) News and Views, *Science,* 1994, 265, p. 2008, 2085, 2096.

[12] Symous, R. H., *Nucleic Acid Probes,* CRC Press, Boca Raton. Fla., 1989.

[13] See for example: Su, H.; Kallury, K. M. R.; Thompson, M. *Anal. Chem* 1994, 66, 769 and references therein.

What is claimed is:

1. A surface coating comprising a self-assemble layer of bola amphiphilic amidine molecules reversibly bound to a substrate by cyclic ion pairs formed by polar interaction between the amidine groups of the bola amphiphilic amidine molecules and anionic groups of the substrate.

2. A surface coating according to claim 1, wherein the polar interaction between the bola amphiphile and the substrate is pH dependent.

3. A surface coating according to claim 1, wherein the amidine is a bisbenzamidines.

4. A surface coating according to claim 3, wherein the bisbenzamidine has a linking group with 2–14 carbon atoms.

5. A surface coating according to claim 4, wherein the bisbenzamidine is selected from the group consisting of ethamidine, pentamidine, octamidine, and decamidine.

6. A surface coating according to claim 5, wherein the bisbenzamidine is pentamidine.

7. A surface coating according to claim 2, wherein the amidine is a bisbenzamidine.

8. A method for preparing a surface coating, comprising providing a substrate with anionic groups;
providing bola amphiphilic amidine molecules;
providing a self-assembled layer of the bola amphiphilic amidine molecules on the substrate by
reversibly binding the bola amphiphilic amidine molecules to the substrate by cyclic ion pairs formed by polar interaction between the amidine groups of the bola amphiphilic amidine molecules and the anionic groups of the substrate, such that the bola amphiphilic amidine molecules coat the surface of the substrate.

9. A method for preparing a surface coating according to claim 8, wherein the polar interaction between the bola amphiphile and the substrate is pH dependent.

10. A method for preparing a surface coating according to claim 8, wherein the amidine is a bisbenzamidine.

11. A method for preparing a surface coating according to claim 10, wherein the bizbenzamidine has a linking group with 2 to 14 carbon atoms.

12. A method for preparing a surface coating according to claim 11, wherein the bisbenzamidine is selected from the group consisting of ethamidine, pentamidine, octamidine, and decamidine.

13. A method for preparing a surface coating according to claim 12, wherein the bisbenzamidine is pentamidine.

14. A method for preparing a surface coating according to claim 9, wherein the amidine is a bisbenzamidine.

15. A biosensor having a substrate with a coating comprising a self-assembled layer of amphiphilic amidine molecules, said amphiphilic amidine molecules having a polar amidine group linked by a non-polar group to a functional group and being reversibly bound to the substrate by cyclic ion pairs formed by polar interaction between the amidine groups of the amphiphilic amidine molecule and anionic groups of the substrate.

* * * * *